(12) United States Patent
Smith et al.

(10) Patent No.: US 9,625,393 B2
(45) Date of Patent: *Apr. 18, 2017

(54) GEMSTONE VIEWER

(71) Applicant: De Beers UK Ltd, London (GB)

(72) Inventors: James Gordon Charters Smith, Buckinghamshire (GB); Michael Peter Gaukroger, Hampshire (GB); Peter Stanley Rose, Buckinghamshire (GB)

(73) Assignee: De Beers UK Ltd., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/885,507

(22) Filed: Oct. 16, 2015

(65) Prior Publication Data

US 2016/0041106 A1 Feb. 11, 2016

Related U.S. Application Data

(63) Continuation of application No. 13/055,518, filed as application No. PCT/GB2009/050862 on Jul. 16, 2009, now Pat. No. 9,188,542.

(30) Foreign Application Priority Data

Jul. 25, 2008 (GB) .................................. 0813654.1

(51) Int. Cl.
*G01B 11/30* (2006.01)
*G01N 21/87* (2006.01)
(Continued)

(52) U.S. Cl.
CPC ............. *G01N 21/87* (2013.01); *G01N 21/01* (2013.01); *G01N 33/381* (2013.01)

(58) Field of Classification Search
CPC ........ G01N 21/01; G01N 21/55; G01N 21/87; G01N 33/381; G01N 2021/555;
(Continued)

(56) References Cited

U.S. PATENT DOCUMENTS 7,315,356 B2 1/2008 Haske
7,355,683 B2 4/2008 Sasian et al.
(Continued)

FOREIGN PATENT DOCUMENTS

CN 101086443 A 12/2007
EP 1 319 942 A1 6/2003
(Continued)

OTHER PUBLICATIONS

Co-pending U.S. Appl. No. 13/055,518 filed on May 17, 2011.
(Continued)

*Primary Examiner* — Christopher Findley
(74) *Attorney, Agent, or Firm* — Renner, Otto, Boiselle & Sklar, LLP

(57) ABSTRACT

An apparatus for viewing images of a gemstone is described. The apparatus comprises a support structure for supporting the gemstone at an observation position. An illumination structure comprises a plurality of directional light sources directed towards the observation position so as to illuminate the gemstone. The support structure and illumination structure are relatively rotatable relative to one another about a rotation axis. An imaging device is arranged to obtain images of the gemstone at the observation position at a variety of relative rotational positions between the illumination structure and support structure: the imaging device has an imaging axis passing through the observation position. The support structure is arranged so that the gemstone can be placed at the observation position in such a way that the normal to a selected facet of the gemstone is within a range of tilt angles from the rotation axis. The arrangement of directional light sources is such that, for any tilt angle within the range, at least one of the directional light sources will be specularly reflected from the selected facet into the (Continued)

imaging device for at least one rotational position of the support structure.

15 Claims, 6 Drawing Sheets

(51) Int. Cl.
*G01N 33/38* (2006.01)
*G01N 21/01* (2006.01)

(58) Field of Classification Search
CPC ....... G01N 2021/556; G01N 2021/557; G01N 2021/559; A44C 17/0258
See application file for complete search history.

(56) References Cited

U.S. PATENT DOCUMENTS

| | | | | |
|---|---|---|---|---|
| 8,035,607 | B2 | 10/2011 | Otome | |
| 8,035,807 | B2 * | 10/2011 | Wagner | G01N 21/87 356/30 |
| 8,319,145 | B2 * | 11/2012 | Rosario | B23K 15/08 219/121.19 |
| 8,598,557 | B2 * | 12/2013 | Cochran | G01N 21/8806 250/559.34 |
| 2005/0213077 | A1 | 9/2005 | Sasian et al. | |
| 2005/0254037 | A1 | 11/2005 | Haske | |
| 2007/0109529 | A1 | 5/2007 | Wagner et al. | |
| 2007/0273885 | A1 | 11/2007 | Njo et al. | |
| 2008/0225266 | A1 * | 9/2008 | Van De Velde | G01N 33/381 356/30 |

FOREIGN PATENT DOCUMENTS

| | | |
|---|---|---|
| EP | 1 764 610 A1 | 3/2007 |
| GB | 2 350 693 A | 12/2000 |
| IL | 176196 | 4/2010 |
| WO | WO 99/34197 | 7/1999 |
| WO | WO 01/14854 A1 | 3/2001 |
| WO | WO 03/103439 A2 | 12/2003 |

OTHER PUBLICATIONS

International Search Report for corresponding International Application No. PCT/JP2009/050862 mailed Oct. 19, 2009.
UK Search Report for corresponding UK Application No. GB0813654.1 dated Nov. 6, 2008.
Official Action dated Jun. 18, 2012 in corresponding Singapore Patent Application No. 201100529-5.
English translation of Official Action issued Dec. 28, 2012 in corresponding Chinese Application No. 200980137409.5.
Second Official Action mailed Apr. 4, 2013 in corresponding Singapore Patent Application No. 201100529-5.
Second Chinese Office Action issued Sep. 10, 2013 in corresponding Chinese Application No. 200980137409.5 and English translation thereof.

* cited by examiner

GEMSTONE VIEWER

FIELD OF THE INVENTION

The present invention relates to an apparatus and method for viewing gemstones. In particular, although not exclusively, the invention relates to an apparatus and method for viewing both the play of light in a gemstone and a mark inscribed on the surface of the gemstone.

BACKGROUND

The beauty or attractiveness of gemstones, and in particular diamonds, is considered to be directly related to how the stones interact with light. This interaction is known as the "play of light" and incorporates properties such as brilliance, fire and scintillation displayed by the stone. Brilliance relates to the intensity and contrast of light returned by the stone to the observer, fire relates to the amount of dispersed light returned by the stone and scintillation relates to the incidence of light flashes visible to the observer as the stone is moved relative to a light source.

Recently the practice of marking gemstones with brand marks, identification numbers, and/or marks conveying other information regarding the gemstone has become more widespread. Marks may be applied to stones using a variety of methods, such as for example those described in WO 98/52774. The marks can be applied in such a way as to be invisible to the eye using a ×10 loupe so that they do not detract from the value or appearance of the gemstone. This means that the marks can be applied to facets such as the table of the stone. Such marks are typically inscribed to a depth of up to about 0.05 µm into the stone.

In the retail environment it would be advantageous to provide a quick, practical and effective viewer that would allow a retailer to display to a customer both the play of light in a gemstone and the inscribed mark.

There are a number of viewers currently available that can be used to view play of light in gemstones. One example of such a viewer is provided in WO 2001/14854. Further viewers can also be used to view marks inscribed in stones, and such a device is described in WO 99/34197 which provides means to view a magnified image of the gemstone and the mark, but does not provide a means of viewing the play of light in the stone. A further viewer is described in EP 1319942 which enables the display of both play of light and a mark. However, due to the difficulty in providing the correct lighting conditions to display the play of light and the mark, the gemstone must be moved from one part of the viewer to another to view these different attributes.

It is known that, in order to display the properties of brilliance, fire and scintillation, varied lighting conditions are required. For example, the level of dispersed light may be hidden by the high level of reflected white light of a very brilliant gemstone under some lighting conditions. Varied lighting conditions may be provided by movable annular lighting such as that employed in the BrillianceScope™ Analyzer that measures the light that is returned through the crown of a diamond when it is illuminated from 6 different angles in a controlled lighting environment. It has also been shown to be advantageous to use multiple directional light sources, such as that produced by a number of LEDs, particularly when displaying the fire and scintillation of a gemstone. EP 1319942 describes an apparatus for determining play of light of a gemstone using a highly symmetrical lighting pattern that can be rotated and whose intensity can be controlled to vary the lighting. This symmetrical lighting system emphasises the symmetry of the stone. However, it is also known that, although highly symmetrically cut stones provide a good predictability for good play of light, stones with a lesser degree of symmetry can give equally good play of light.

Similarly, U.S. Pat. No. 7,315,356 provides an apparatus for imaging the fire of a gemstone where the varied lighting is provided by a symmetrical lighting pattern. It has been found that using a highly symmetrical lighting pattern does not provide adequate means for visual appreciation of the play of light for the majority of stones.

The present invention aims to overcome or at least alleviate one or more of the difficulties associated with the prior art.

SUMMARY

In accordance with one aspect of the present invention there is provided an apparatus for viewing images of a gemstone. The apparatus comprises a support structure for supporting the gemstone at an observation position. An illumination structure comprises a plurality of directional light sources directed towards the observation position so as to illuminate the gemstone. The support structure and illumination structure are relatively rotatable relative to one another about a rotation axis. An imaging device is arranged to obtain images of the gemstone at the observation position at a variety of relative rotational positions between the illumination structure and support structure: the imaging device has an imaging axis passing through the observation position. The support structure is arranged so that the gemstone can be placed at the observation position in such a way that the normal to a selected facet of the gemstone is within a range of tilt angles from the rotation axis. The arrangement of directional light sources is such that, for any tilt angle within the range, at least one of the directional light sources will be specularly reflected from the selected facet into the imaging device for at least one rotational position of the support structure.

Thus, as the gemstone is rotated on the support structure (or the illumination means is rotated relative to the gemstone), the play of light in the gemstone can be attractively displayed to the user. In addition, there will be at least one rotational position in which a specular reflection from one of the directional light sources will be directed into the imaging device from the selected facet (which will usually be the table facet). If a mark is inscribed in this facet, an image of the mark can be obtained—and displayed to the user—when the gemstone is at this rotational position. Thus both the play of light in the gemstone, and a mark inscribed on the gemstone, can be displayed to a viewer without the need to remove the gemstone from one place to another. All of the elements described above, together with a display screen may be integrated together into a single instrument into which the gemstone can be placed.

Furthermore, since the normal to the selected facet need only be within a range of tilt angles (for example less than 5°, or even less than 10°) relative to the rotational axis of the support structure, accurate placement of the gemstone on the support structure is not necessary. The gemstone could, for example, be mounted in a ring placed within a ring box. As long as the table of the gemstone is roughly horizontal (for example less than about 20-25° to the horizontal), as it rotates there will still be at least one position in which an image of the mark can be obtained by the imaging device. Alternatively, the gemstone could be a loose gemstone, placed in a mount so that the table is uppermost. Again, even if the alignment is approximate, there will be at least one rotational position at which a mark inscribed on the table can be viewed. Any of the methods of supporting a loose gemstone or supporting a gemstone in a jewelry setting which are well known to the skilled artisan may be employed.

The illumination structure may also include a diffuse light source so that the whole gemstone is illuminated, rather than just individual scintillations. The directional light sources and/or diffuse light source may be white light sources and may include white LEDs. The diffuse light source may include a diffuser, which may have apertures comprising holes or clear areas of material therethrough to allow light from the directional light sources to pass through. The directional light sources may include LEDs with collimating lenses providing at least a degree of collimation of the light. The collimating lenses may be attached to the LEDs or attached or incorporated into the diffuser.

Although it is possible to rotate the illumination structure and leave the gemstone stationary, it has been found that it appears more natural to a customer if the gemstone itself rotates. In this case, the support structure may include a rotary table. It is also beneficial for the customer to be able to see the gemstone directly while images are simultaneously displayed on a screen. The support structure may also be moveable towards and away from the imaging device.

The directional light sources can be arranged in a symmetrical pattern, but as discussed above this approach tends to favour only highly symmetrical diamonds. In one embodiment, therefore, the directional light sources are arranged in a pattern which does not have 4-fold or 8-fold rotational symmetry. Since it is desirable that the images of the gemstone should be presented attractively to the customer, the directional light sources may be arranged generally uniformly across the illumination structure.

The requirement that an image of at least one specular reflection is obtained can be approached as follows. A locus can be visualised on the illumination structure of a reversed ray reflected in the selected facet from the imaging device for a 360° rotation of the support structure with the facet at any given tilt angle. The directional light sources may then be arranged so that, for every tilt angle within the range of tilt angles, at least one of the directional light sources is located on the locus for that tilt angle.

The directional light sources may be arranged in a spiral pattern. This can be effected, for example, by advancing the phase of directional light sources on successive loci, for example by 90° (which leads to 4-fold symmetry) or by the "golden angle" of 137.5°, although it will be appreciated that other angles may also be suitable.

The illumination structure may be arranged generally between the imaging device and the observation position, with a hole in the illumination structure to enable light to pass from the observation position to the imaging device. The illumination structure may be generally planar or may in some arrangements form a curved plane or spherical section. The imaging axis of the apparatus may be equilinear to the rotation axis of the support structure, or may be inclined, for example at an angle between 0° and 45° or 0° and 5°. If the imaging axis and rotation axis are equilinear it may be necessary to provide a virtual directional light source to direct directional light along the imaging axis. This may be achieved by the use of a beam splitter, for example.

The imaging device of the apparatus may produce images of the gemstone formed by a lens, which may be varifocal and may include autofocusing. The imaging device may also include a camera such as a CCD or CMOS camera. The imaging device and the lens of the apparatus may comprise a single module. The lens may have a range of magnifications and/or the camera may be provided with sufficient picture elements (pixels) to allow digital zoom.

A processor may be provided for analysing the images obtained by the imaging device and identifying the rotational position at which one of the directional light sources is specularly reflected from the selected facet into the imaging device so that the image of the mark can be obtained. The processor may be operatively connected to a control system for controlling the relative rotation between the support structure and the illumination structure. The control system can then be configured to ensure that the support structure is moved to the appropriate rotational position for the image of the mark to be displayed to the customer only after the images illustrating the play of light in the gemstone have been displayed to the customer. The control system may also be adapted to control the operation of the directional light sources, and the processor adapted to identify which directional light source is specularly reflected in the selected facet when the support structure is at the appropriate rotational position. This enables control of the directional light sources so that the image of the mark can be "suppressed" until the end of the sequence, and also enables the mark to be displayed as clearly as possible by ensuring the use of the correct directional light source. A recording system may also be employed to record an image or series of images of the play of light of the gemstone and the mark inscribed on the gemstone.

In accordance with another aspect of the present invention there is provided an apparatus for generating and viewing images of the play of light in a loose or mounted gemstone and an inscribed mark on the gemstone in a single integrated unit. The apparatus comprises a support means for supporting the gemstone in an observation position. Illumination means are provided for illuminating the gemstone in the observation position, the illumination means comprising a plurality of directional light sources and a diffuse light source. Rotation means are provided for rotating the support means relative to the illumination means. Imaging means are provided for obtaining images of the gemstone in the observation position. Display means are provided for displaying the images of the gemstone to an observer at a plurality of rotational positions of the support means.

The invention also provides a method for facilitating the visual appreciation of the play of light of a loose or mounted gemstone and an inscribed mark, comprising viewing the gemstone using any version of the apparatus described above.

In accordance with another aspect of the present invention there is provided a method for facilitating the visual appreciation of the play of light of a loose or mounted gemstone (such as a diamond) and a mark inscribed on a selected facet (usually a table facet) of the gemstone. The gemstone is illuminated with a plurality of directional light sources, and rotated about a rotation axis relative to the plurality of directional light sources. The normal to the selected facet of the gemstone is within a range of tilt angles from the rotation axis. Images of the gemstone are obtained as the gemstone rotates, and these images are displayed to an observer. The arrangement of directional light sources is such that, for any tilt angle within the range, at least one of the directional light sources is specularly reflected from the selected facet into the imaging device for at least one rotational position of the gemstone. An image of the inscribed mark may be displayed to the user by rotating the gemstone to the rotational position at which one of the directional light sources is specularly reflected from the selected facet into the imaging device. The gemstone may also be viewed by eye as it is illuminated or rotated.

Thus the present invention, at least in some embodiments, provides an apparatus and method for facilitating the visual appreciation of the play of light of a loose or mounted gemstone and an inscribed mark in a single integrated unit. The unit can be manufactured as a single integrated system that requires little skill or training to use.

Furthermore, some embodiments of the invention provide an apparatus and method for viewing a loose or mounted gemstone comprising the following elements:
1. Displaying the play of light of a gemstone so that it can be seen directly by eye.
2. Generating a magnified image of the gemstone to display the play of light.
3. Generating a magnified image of the gemstone to display an inscribed mark.

Some embodiments of the invention provide an apparatus and method for viewing and generating an image of the play of light of a gemstone and a mark irrespective of the degree of symmetry of the gemstone.

PREFERRED EMBODIMENTS

Some preferred embodiments of the invention will now be described by way of example only and with reference to the accompanying drawings, in which.

GENERAL ARRANGEMENT

Figure 1:
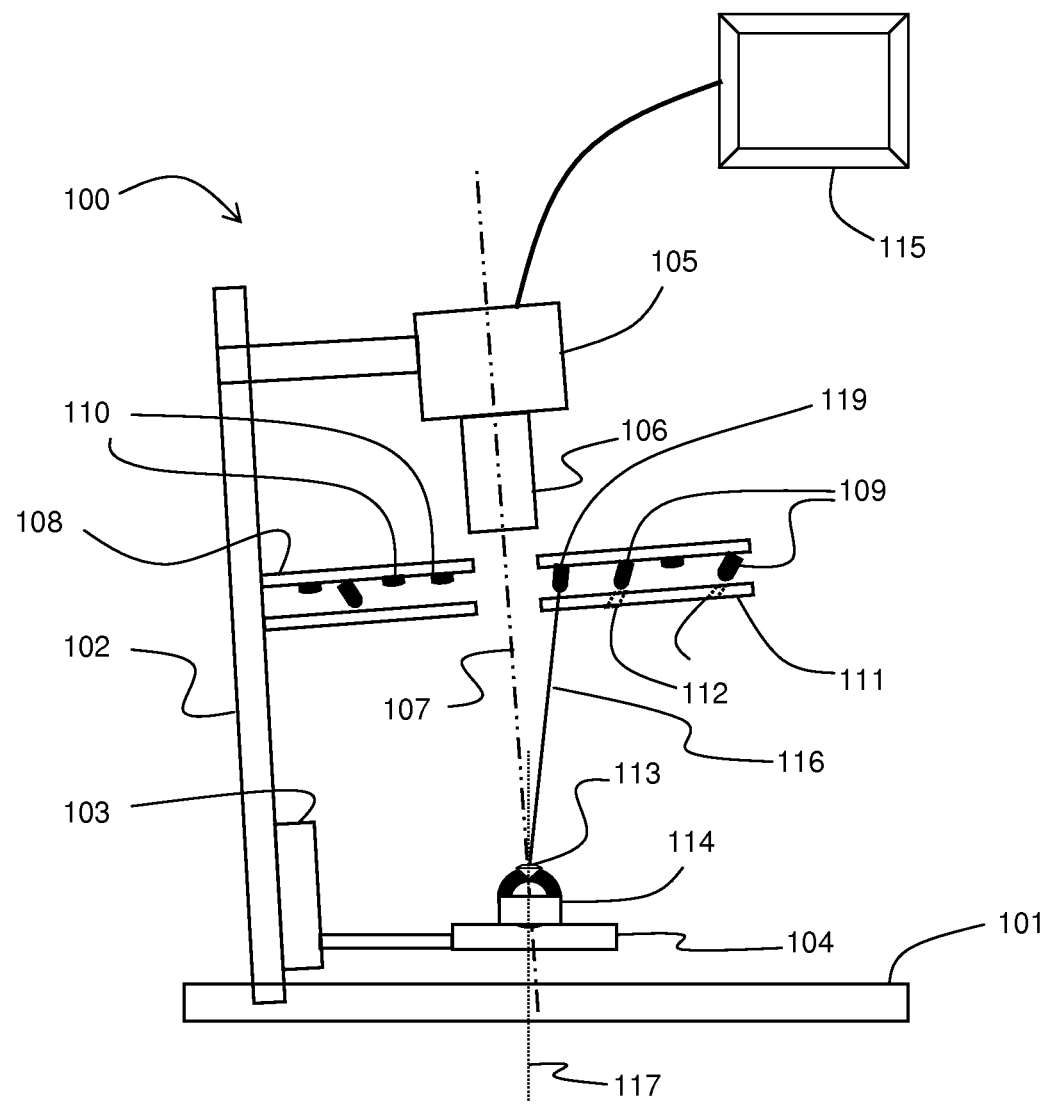
FIG. 1 is a schematic view of a viewer for displaying play of light in a gemstone and a mark inscribed on a gemstone.

FIG. 1 shows a schematic diagram of a viewer 100. The structure of the viewer is formed by a base 101 and support member 102 which is generally (although not necessarily exactly) perpendicular to the base. A linear slide 103 is movably mounted on the support member 102 so that it can move along the support member 102. A rotary table 104 is supported by the linear slide 103.

The surface of the rotary table 104 is preferably parallel to the base 101, and in normal operation the base 101 would be placed on a substantially horizontal surface such as the counter of a jewelry store. Thus references to horizontal and vertical in this description refer to directions parallel and perpendicular to the underside of the base 101.

An imaging device 105 such as a camera having a lens assembly 106 is mounted on the support 102 such that it points towards the rotary table 104 along an imaging axis 107, which should be parallel to the support member 102. The linear slide 103 thus allows the rotary table 104 to be moved towards or away from the imaging device 105 along the imaging axis 107. The imaging axis 107 is preferably inclined to the vertical by an angle of, for example 5°, although any angle of between 0° and 45° might be employed.

The lens assembly 106 comprises a plurality of refracting elements and is typically provided with internal mechanical motions that can alter the magnification between an object placed on the rotary table 104 and the imaging device 105, and adjust focus. Such lenses are commonly known as zoom or varifocal lenses. The imaging device 105 and the lens 106 may be a single module such as a Sony block camera combined with an auxiliary close up lens element.

In an alternative embodiment or in addition, the imaging device 105 may be provided with more picture elements (pixels) than is required to produce an image of acceptable quality so that the technique commonly known as digital zoom may be employed.

The viewer is also provided with an illumination structure 110, which may be characterised as combining two classes of lighting elements. One set provides a plurality of directional elements and a further set may provide a diffuse background. Any convenient light sources may be used. In one embodiment white light sources such as white Light Emitting Diodes (LEDs) are employed.

As shown in FIG. 1, the illumination structure 108 generally takes the form of a flat disc around the imaging axis 107, and comprises a set of directional LEDs 109 and a set of background LEDs 110, located above a diffuser 111. The diffuser 111 scatters the light propagating from the background LEDs 110 so as to provide a diffuse illumination to an object placed on the rotary table 104. Holes (or clear apertures) 112 in the diffuser 111 in front of each of the directional LEDs 109 allow directional illumination from the centre of each directional LED 109 to reach an object on the rotary table 104.

In use, a gemstone 113 such as a gem diamond is supported in a gemstone support 114 and placed on the rotary table 104 on the imaging axis 107. An image of the diamond 113 can then be formed in the imaging device 105 by the lens 106. The gemstone 113 is rotated by rotation of the rotary table 104, and can be moved towards or away from the lens 106 by use of the linear slide 103. An image of the rotating diamond is displayed on a screen 115. This enables a user to see a magnified view of the gemstone 113 as it rotates, and this shows off the play of light in the diamond to great effect.

The gemstone 113 will usually be a polished diamond, such as a round brilliant cut diamond, but it will be appreciated that other diamond cuts (or other gemstones) may also be viewed. The gemstone will generally have a major planar facet known as the table facet as its uppermost surface, and should be oriented so that this facet is as near to horizontal as possible. The normal to the table facet should usually make an angle of less than 22.5° to the vertical, and should be as close to 0° to the vertical as is practical.

The gemstone support 114 may be any support means that allows the gemstone 108 to be supported on the rotary table 104. If the gemstone 113 formed part of a jewelry ring such as an engagement ring, the gemstone support 114 would consist of the ring itself with the gemstone 113 mounted in it and, for example, a ring box that might also be used to display the ring in a store.

Control and Feedback

In operation it is advantageous for suitable control means such as a microprocessor and suitable driver circuitry (not shown) to be able to have independent control of each of the directional LEDs 109. The brightness of each may be adjustable either by controlling the current each draws, or by the technique of pulse width modulation. In addition the background LEDs 110 should have a similar control channel, common to all of the diffuse LEDS.

The control means should also be able to control the motion of the linear slide 103 and the rotary table 104 to alter the relative position of the gemstone 113 and the lens 106. Motion of the linear slide constitutes a focus adjustment.

The control means should also have control over the operation of the imaging device 105 and the lens 106. Without limitation, these controls would cover the aperture stop of the lens 106, the exposure time of the imaging device 105 and the gain, colour balance, contrast and brightness and any image sharpening provided in the imaging device 105. It may be that the lens 106 is provided with a focus adjustment that can be controlled automatically by the imaging device 106 or by the control means.

Image data produced by the imaging device 105 may be displayed directly on a screen 115, such as a flat panel video monitor integrated into a housing (not shown) of the apparatus. For example, images of the gemstone 113 could be viewed simultaneously by a customer and a sales-person concerned with the potential purchase of the gemstone 113.

It would be useful for some feedback to be provided so that the control means may make appropriate adjustments in order to obtain an attractive image sequence or video beneficial to the sales process. In its simplest form the sales-person could provide the feedback by evaluating the images and making adjustments to the various controls.

However it is preferable that the feedback is provided within the apparatus so that, once a start stimulus has been supplied, the apparatus carries out a predefined demonstration without further intervention. The apparatus may analyse the image data generated by the imaging device 105, by capturing image frames into computer memory (not shown) using a frame grabber or by direct use of an imaging device that produces a digital video signal. The image may be analysed and modified by data analysis and processing means. The displayed image may be of the original image data or that captured and modified by the data processing means (not shown).

As an example, and without limitation, the data processing means may split the image into separate red, green and blue channels, and calculate a histogram for each channel. The histogram may be used to identify the range of light levels apparent in each channel. These histograms may be compared with target values and used to adjust, for example the lighting level using either the directional or diffuse LEDs 109, 110. Further data processing may be used to identify the region of the image occupied by the gemstone 113, and if the image size were, for example too small, the control means may adjust the zoom setting of the lens 106 to provide more magnification.

In order to obtain further information the control means may alter the light level produced by a particular directional LED 109 and the data processing means may determine the effect of this by examining changes in the resulting image. This information may be associated with a particular position or range of positions of the rotary table 104 so that, for example, the system will know that a particular directional LED 109 produces a bright reflection from the table facet of the gemstone 113 over a known range of rotational positions of the rotary table 104. This information, which may be stored in an appropriate data structure within the data analysis or control means, may be used later in the process either to suppress or to emphasise the reflection from the table facet.

Illumination

While any suitable arrangement of illuminating elements may be employed, it should have certain properties to ensure that the diamond gem is presented in attractive manner under different circumstances, which may be selected from, but are not limited to:

Providing illumination so that the gemstone and jewelry are presented attractively to an observer viewing the gemstone directly;

Providing illumination so that an attractive image containing the gemstone and possibly the jewelry may be viewed on the display screen of the apparatus or another screen;

Providing illumination so that a facet and, if present, an inscription etched into said facet may be viewed by a specular reflection, without requiring any precision alignment of the orientation of the facet to be viewed.

In other words, it should be possible to provide an attractive display to the user, either on the screen 115 or directly, as the gemstone 113 rotates on the rotary table 104. It should then be possible to display to the user an image of a mark inscribed on the gemstone, using the same illumination system and without any need to move the gemstone from the rotary table.

The dual arrangement of directional LEDs 109, together with background LEDs 110 and diffuser 111, assists in meeting these conditions. The directional LEDs 109 act as "point sources" illuminating the gemstone 113. Light reflected from these point sources into the imaging device 105 will appear in the image of the gemstone 113 as scintillations and will cause the gemstone to appear to "sparkle". Light from the directional LEDs 109 will also be reflected out of the instrument and directly towards the observer, who will see the gemstone 113 sparkling both in the image on the screen 115 and directly "in the flesh".

As will be explained in more detail below, under certain circumstances light from one of the directional LEDs 109 will also be specularly reflected from the table facet of the gemstone directly into the imaging device 105. This will enable a mark inscribed in the table facet to be viewed on the screen 115.

If the gemstone 113 is illuminated only by the directional LEDs 109, it can sometimes appear as a generally dark image with a few spots of light. The background LEDs 110 and diffuser 111 provide a diffuse light that illuminates the whole of the gemstone 113 so that it appears much brighter in the image displayed on the screen 115. The combination of the two lighting effects results in a much more attractive image of the gemstone 113.

It will be understood that the diameter of the holes 112 in the diffuser 111 will have an effect on the apparent position of the light sources of the directional LEDs 109. These holes may be smaller in diameter than the directional LEDs, in which case the sources will appear to be located at the holes rather than at their real positions. Further optical elements may be provided between the directional LEDs 109 and the gemstone 113. One effect of these elements will be to alter further the apparent position of the directional LED sources.

In one embodiment the directional LEDs 109 are positioned so as to contribute to the attractive appearance of the gemstone under direct viewing and on the display screen, while also ensuring that a specular reflection at the table facet from at least one of the directional LEDs 109 will enter the imaging means 105 for at least one orientation or range of orientations of the rotary table 104, without requiring any precise alignment of the orientation of table facet.

It will be appreciated that the attractiveness of the diamond image is a subjective aspect while the observation of an inscribed mark to be made visible in a rotary cycle is a more objective criterion. This latter criterion places constraints on the arrangement of lighting which are now described with reference to FIG. 1.

Essentially, an inscribed mark can be seen by the imaging device if a specular reflection from the facet in which the mark is formed is directed into the imaging device 105. A specular reflection will be observed from a facet of the gem diamond 113 if a ray of light 116, originating at a particular directional LED 119 and incident onto the facet and reflected according to the laws of reflection of light, is directed along the imaging axis 107.

Equivalently, the condition for a reflection to be observed is satisfied if a fictitious reversed ray of light, travelling along the imaging axis 107 from the imaging device 105 towards the gemstone 113 and reflected from the table facet of the gemstone 113, leads to one of the directional LEDs 119.

FIG. 1 illustrates a relatively rare situation where, perhaps by chance, the normal to the table facet of the gemstone 113 has been placed parallel to the rotation axis 117 of the rotary table 104. In this case, the direction of the reversed ray 116 that is shown leading to one of the directional LEDs 119 is not altered by the rotation of the rotary table 104 and will always lead to that particular directional LED 119 which can be called the "central" LED 119 of the pattern.

In general the gemstone 113 will not be so aligned and, as the rotary table 104 rotates, the reversed reflected ray 116 would describe an approximately circular locus on the underside of the diffuser 111, the centre of the locus being located approximately at the central LED 119.

It will be understood that the exact shape of the locus will depend on the detailed geometry of the apparatus. For the case shown, where the sources appear to located in a plane at the underside of the diffuser 111, the locus on that surface would be a conic section, and this may be constructed in accordance with the principles described above.

For small tilts between the rotation axis 117 and the surface normal of the reflecting facet, the reversed reflected ray will continue to intersect the central LED 119, and a specular reflection will continue to be observed. But as the angle is increased the locus of the reflected ray will no longer intersect the central LED 119 and the specular reflection will not occur from this source.

Instead, at least one further source must be positioned to intersect this locus so that, during the rotation of the rotary table, the locus of the reversed reflected ray 116 will intersect at least this further source.

Each source 109 will provide illumination for a specular reflection at some point during the rotation of the rotary stage 104, for a certain range of angles between the gemstone surface normal and the rotation axis 117. This means that a figure can be constructed consisting of a series of approximately circular rings, the spacing between the rings depending on the size of the directional sources, on the underside of the diffuser 111.

Figure 2:
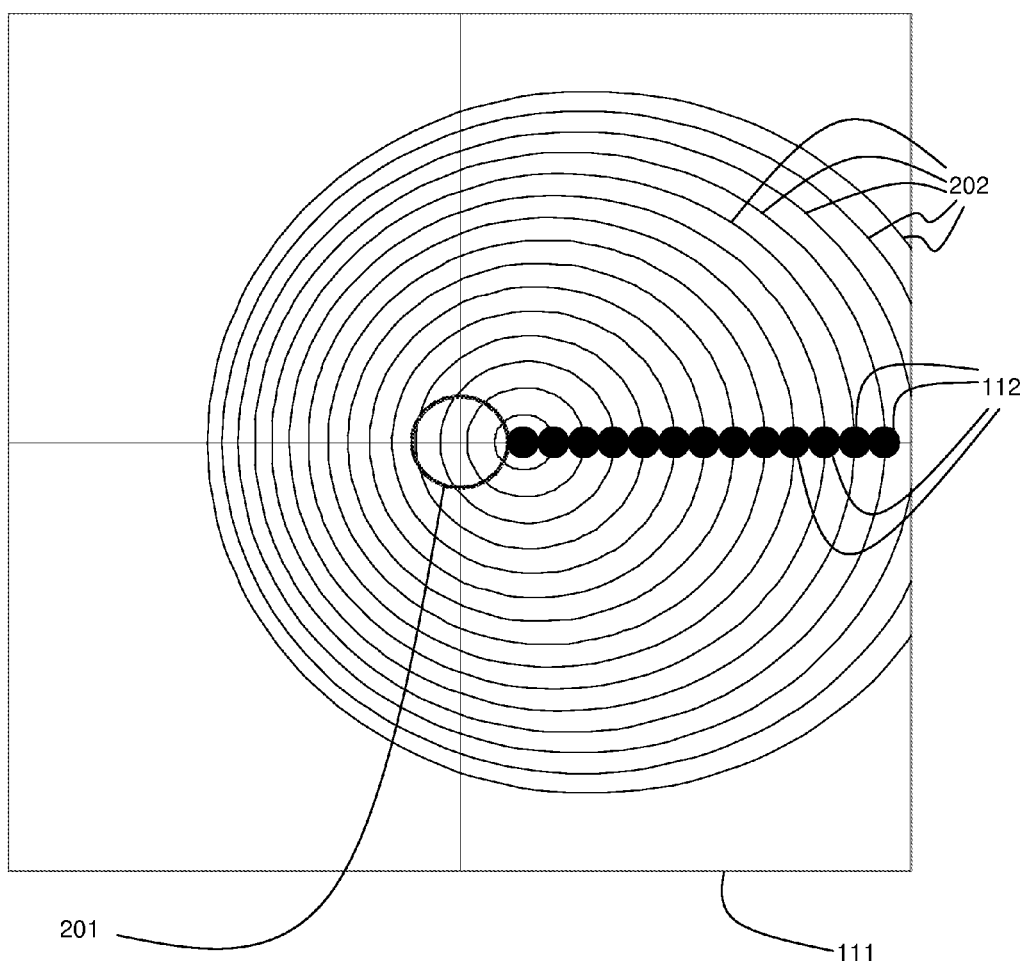
FIG. 2 is a schematic view of an arrangement of directional light sources.

This is illustrated in FIG. 2 which shows, in schematic form, the underside of the diffuser 111 and the directional sources defined by the apertures 112 in the diffuser 111. A circle 201 in the centre of the figure represents the hole in the centre of the disc through which light from the lens 106 passes, and defines a region where it is not possible to place source LEDS without introducing beam splitters or similar.

A set of nested approximately circular curves 202 represent the loci of a reversed ray, originating along the imaging axis 107 and reflected from the table facet of the gemstone 113, for a complete rotation of the rotary table 104, for a range of tilt angles between the rotation axis 117 of the rotary table and the normal to the table facet of the gem diamond. The figure shows one possible arrangement of apertures 112 (each of which will have a directional LED 109 behind) in a straight line. It will be noted that the apertures 112 (and LEDs 109) also have a finite size and do not act as perfect point sources. Provided at least one directional LED 109 is positioned on each curve 202, and the maximum spacing between adjacent rings is less than the apparent diameter of the source LEDs 109, at least one specular reflection from the table facet will be observed during the rotation of the rotary table.

It will be understood by those skilled in the design of optical instrumentation that the criterion for the observation of a reflection should properly take into account the convolution of both the source LED aperture 112 and the optical aperture of the lens 106, but in practice this elementary treatment, which only considers the illumination of principal or chief ray provides sufficient guidance to assemble an apparatus according to the invention.

It will be noted that, although FIG. 2 shows a possible arrangement of the source LEDs 109, the source LEDs 109 are not distributed approximately uniformly over the surface of the diffuser, but are all on one side. This arrangement will ensure that a mark inscribed on the table facet of the gemstone 113 can be viewed at at least one rotational position, but will have a detrimental influence on the appearance of the diamond, particularly the arrangement of scintillations within the diamond, such that they may not appear to be distributed uniformly over the surface of the diamond when viewed via the imaging device 105 but may appear grouped to one side or in a generally unpleasing disposition.

Figure 3:
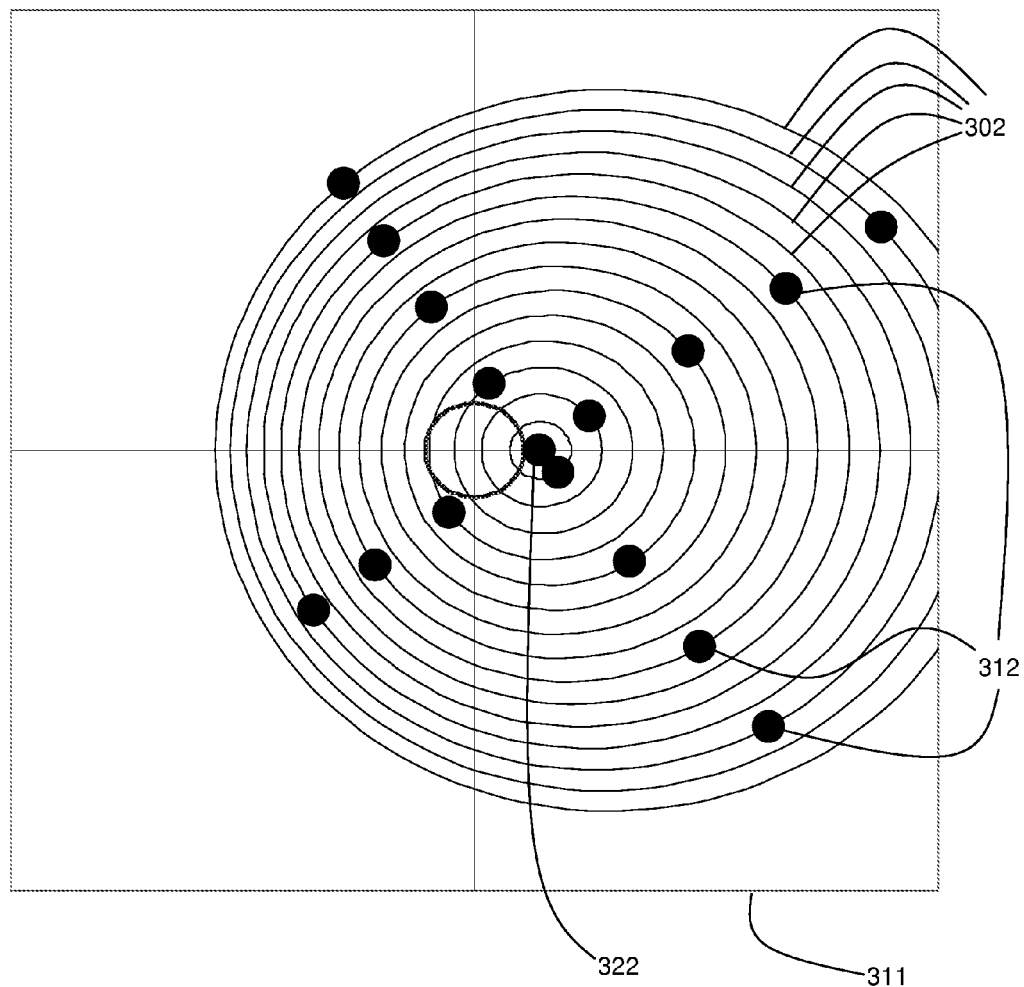
FIG. 3 is a schematic view of an alternative arrangement of directional light sources.

An alternative arrangement is illustrated in FIG. 3, showing the underside of an alternative diffuser 311. Here the positions of each aperture 312 and associated directional LED have been altered so that they are no longer in a line but are distributed in a more balanced fashion. The pattern will still meet the general requirement that a specular reflection from the table facet of the diamond can always be seen. This has been obtained by placing the apertures 312 in successive rings 302 so that they correspond to reflections generated by advancing the angle of the rotation of the rotary stage 104 by 90° for each increase in gemstone table facet tilt angle. This may be referred to as a phase advance of 90° between successive rings 302, and the pattern so produced may be referred to as a spiral with an advance angle of 90°.

This example possesses a degree of 4 fold symmetry about an axis centred on the central LED and associated aperture 322. If it were desirable this symmetry could be enhanced further, purely for example, by placing 4 directional LEDs on each of the circles 302 and/or, as will be discussed later, reducing or eliminating the tilt between the axis of rotation 117 of the rotary stage 104 and the imaging axis 107, to produce a more symmetrical viewing and lighting distribution.

The effect of illuminating the gemstone with a symmetrical light distribution, especially one possessing similar symmetries to the faceting pattern of the gemstone 113, is to produce a symmetrical pattern of scintillations or highlights in the image, provided the gemstone has been polished very accurately. This degree of accuracy in polishing, which may go beyond that needed, for example to obtain an excellent symmetry grade on a grading certificate, may be described by the general term "optical symmetry".

Gem diamond cuts, such as the round brilliant cut or the Princess cut, often possess at least a four-fold symmetry, so a pattern of illumination with four-fold symmetry, such as the example described with reference to FIG. 3, is likely to show a strongly symmetrical pattern in diamonds with good optical symmetry.

The benefit of a diamond with high optical symmetry is a subject of controversy or debate within the diamond trade. If the view is taken that a high degree of optical symmetry is desirable, it would be preferred to arrange the illumination in a symmetrical manner, for example, in accordance with FIG. 3, so the degree of optical symmetry may be demonstrated.

However, most polished diamonds are not produced to the exacting tolerances needed to obtain a high degree of optical symmetry. While this might be interpreted as a general acceptance of poor workmanship, it can also be argued that the beauty or attractiveness of a gem diamond is related to how the diamond interacts with light in general, and not how it appears under a specifically contrived illumination and viewing arrangement designed to emphasise optical symmetry. In such diamonds the accuracy of faceting, provided it is not too variable, is sufficient to produce an attractive diamond at an economic cost.

Thus in some circumstances it would be desirable to provide illumination that may be considered to be natural or uncontrived, lacking any obvious symmetry that would interact with the optical symmetry of the stone. An exemplary arrangement is illustrated in FIG. 4, which may be compared directly to FIGS. 2 and 3.

Figure 4:
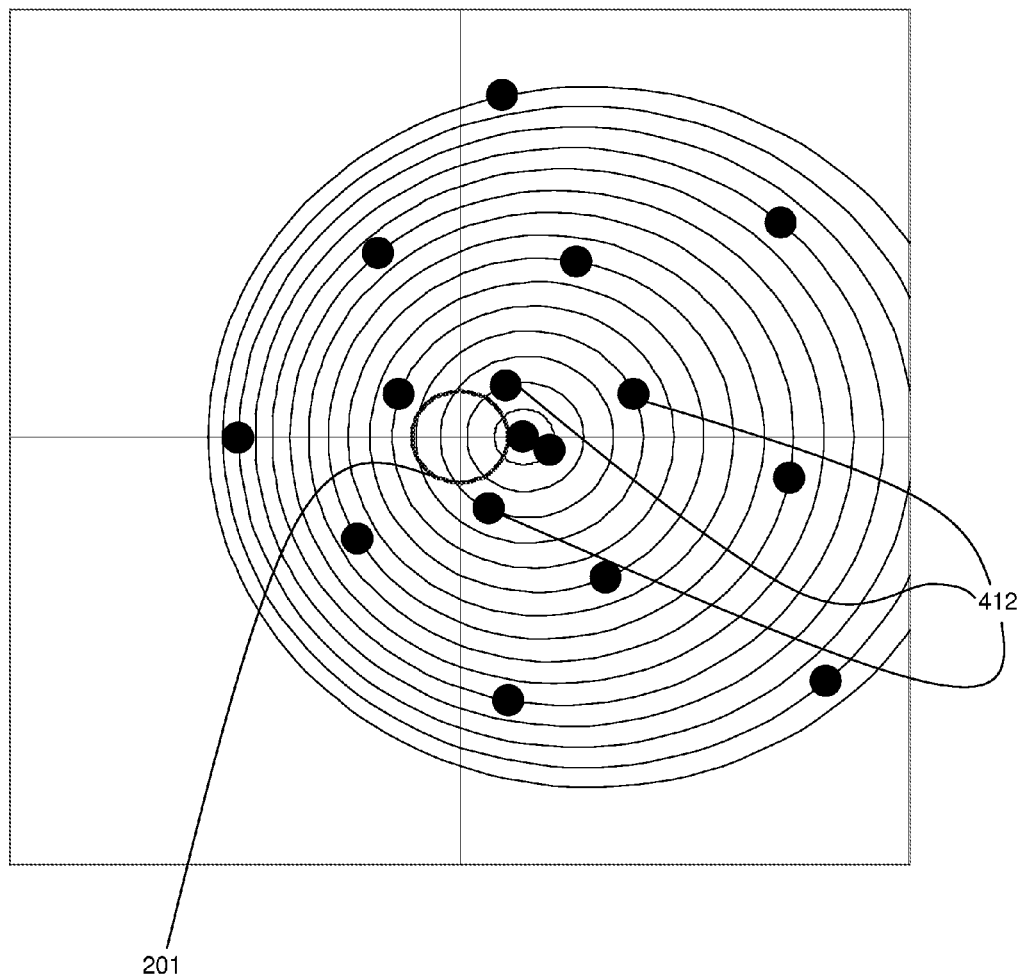
FIG. 4 is a schematic view of another alternative arrangement of directional light sources.

In FIG. 4, successive LEDs behind apertures 412 are advanced in phase by approximately 137.51°, an angle commonly referred to as the golden angle. This angle, which is encountered in natural growth forms such as in spiral phyllotaxis, ensures that successive source LEDs are arranged reasonably uniformly about an axis, while ensuring that no simple symmetries, such as 4-fold or 8-fold, are present in the lighting arrangement that might emphasise the optical symmetry of the diamond.

Although the use of the golden angle in the arrangement of the directional LEDs is effective in producing a balanced natural illumination, it will be appreciated that other arrangements are also possible, and apparatus may be assembled with any arrangement of the directional LEDs, provided the appearance of obvious 4 or 8 fold symmetries is avoided. For example a random or arbitrary phase for each successive ring may be employed.

FIGS. 2-4 illustrate the role of introducing a tilt between the imaging axis 107 and the rotation axis of the rotary stage 104. By moving the central LED and associated aperture away from imaging axis, and by judicious placing of the other directional LEDs, it is possible to avoid placing any sources within that part 201 of the diffuser 111 through which the imaging system 105, 106 views the gem diamond, while ensuring that the specular reflection of the table will be made visible. While this arrangement has this advantage, other arrangements producing the a similar technical effect may be used.

Figure 5:
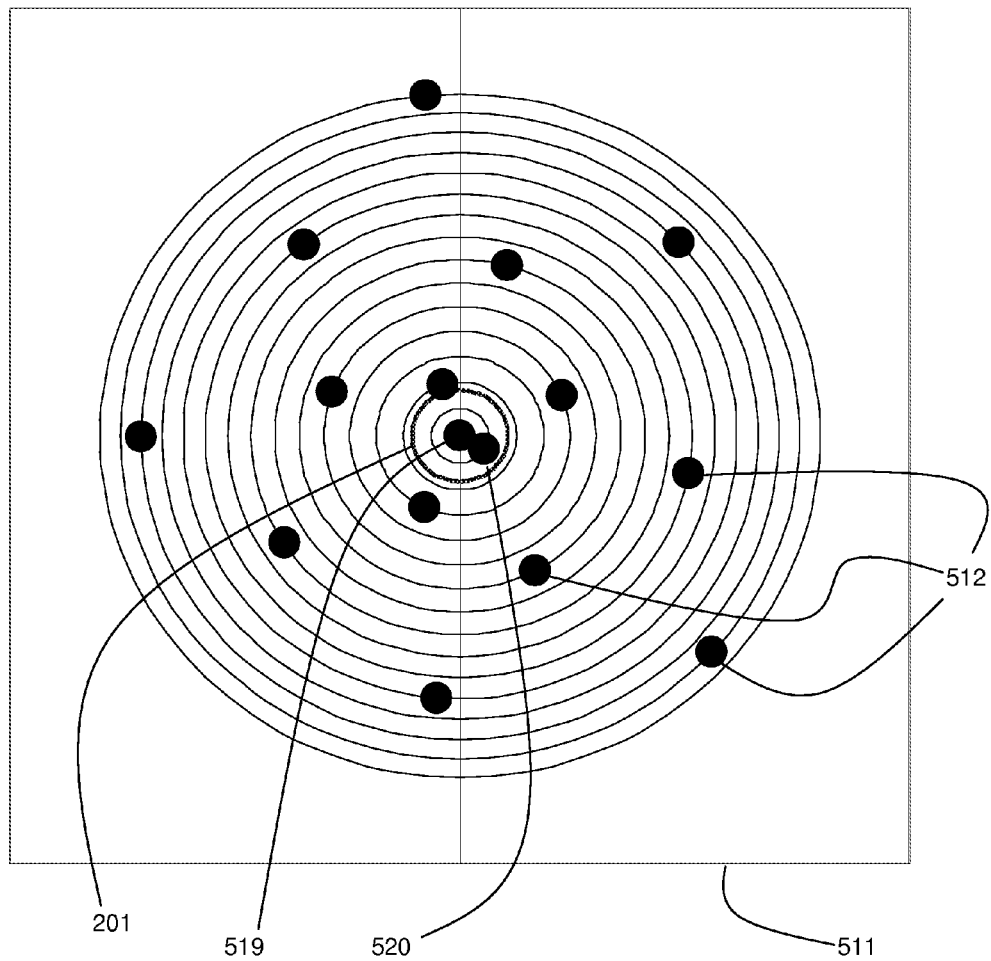
FIG. 5 is a schematic view of a further alternative arrangement of directional light sources.

FIG. 5 illustrates a diffuser 511 for use in a system in which the rotational axis 117 of the rotary table has been made parallel to the imaging axis 107, but the arrangement of FIG. 4 is retained so that LEDs behind their associated apertures 512 are formed in a spiral. The central LED 519 now falls in the centre of hole 201 in the diffuser 511, and thus in front of the lens 106 along the imaging axis, and this directional LED 519 would also obstruct the view of the camera system 105, 106.

It will be appreciated that, despite this problem, a system in which the imaging axis 107 and rotational axis 117 are co-incident can be implemented in a number of ways. For example, the two central LEDs 519, 520 may simply be omitted, although this would leave a risk that, while the diamond may be viewed in a generally attractive manner, an inscribed mark would not be seen if the diamond table facet normal were too close to parallel with the imaging axis 117. This arrangement is simple but runs the risk that the operator would have to reposition the stone to allow the mark to be viewed, to the detriment of the overall quality of presentation.

Figure 6:
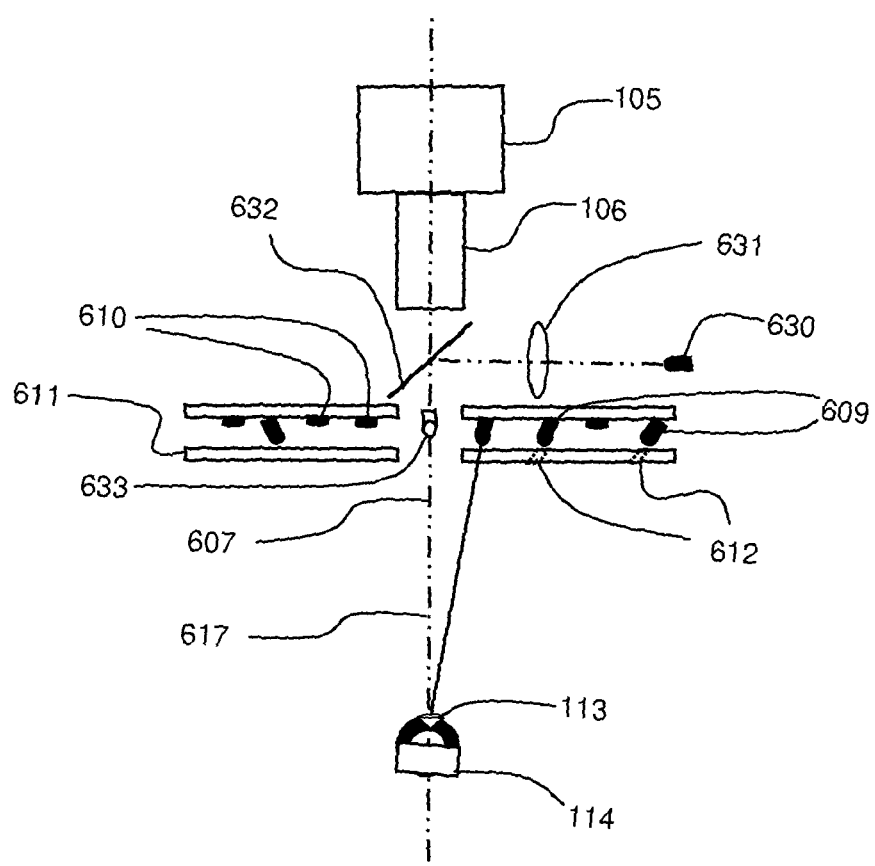
FIG. 6 is a schematic view of an alternative viewer.

Alternatively any missing directional LEDs can be projected into the optical system and a suitable arrangement for putting this into effect is illustrated in FIG. 6. The arrangement of FIG. 6 is similar to that of FIG. 1, although the base, support, linear slide and rotary table are not shown in the figure. The illumination structure is again a combination of directional LEDs 609 and background LEDs 610 located behind a diffuser 611 having apertures 612, although now the imaging axis 607 and rotational axis 617 are coincident.

An additional directional LED 630, relay lens 631 and beam splitter 632 are provided. The relay lens 631 forms an projected image 633, preferably at approximately unit magnification, of the additional directional LED 630. The beam splitter 632 allows a portion of this image to be projected along the imaging axis 607 so that the image 633 occupies the position in space that would have been occupied by the real source LED 630 had it actually been in the centre of the diffuser 611.

Entrance Pupil Matching

Referring back to FIG. 1, in general, the optical system formed by the imaging device 105 and the lens 106 will have an entrance pupil located along the imaging axis. This is an image of the aperture stop of the lens 106. The location and size of the entrance pupil has an important influence on the nature of the images formed by the apparatus. It is helpful to arrange the reflection of the entrance pupil in the table facet of the gemstone 113 to coincide substantially with the apparent position of the directional LEDs 109.

If the lens 106 is a zoom lens, it is likely that the entrance pupil will move as the zoom settings are adjusted. In practice, pupil matching is most important when viewing an inscribed mark and this is usually carried out at the highest magnification. Thus in one embodiment the entrance pupils are matched to the illumination towards the high magnification end of the zoom range and the condition is relaxed at lower magnifications. An advantage of this approach is that a wider field of view may be obtained than the diameter of lens 106.

Since the table facet of the gemstone 113 may be presented over a range of angles, the accurate matching of the directional illumination would require the directional LEDs 109, or their apparent positions, to be on a spherical surface centred on the gemstone 113, rather than on a planar surface as shown in FIG. 1. This is a compromise introduced into the design, for ease of manufacture, recognising that, in practice the gemstone 113 will be placed on the rotary table 104 so that its table facet is reasonably horizontal, so that usually it will be found that it is the directional LEDs 109 nearer the optical axis that will be used to reveal the mark. The error in pupil matching for these LEDs is negligible.

Example

An experimental apparatus broadly according to FIG. 1 was assembled. The base 101 was made of aluminium alloy plate and the support member 102 and other parts, from aluminium alloy extrusions, brackets and the like. The support member 102 was inclined at an angle of 5° to the vertical.

The linear slide 103 was supplied by Aerotech Ltd of Reading Uk—model ATS 302MM with 50 mm of travel.

This was powered by a size 23 stepper motor and a SimStep single axis stepper system supplied by McLennan Servo Supplies Ltd. of Surrey UK. The SimStep single axis was controlled via an RS232 interface from a IBM personal computer (PC).

The rotary table 104 was assembled by mounting a rigid disc of high density polyurethane foam on the output shaft of a Maxon 2325.915-11.111 dc motor fitted with a reduction gearbox of reduction ratio of 400:1. The motor speed and direction were controlled manually using the voltage control knob on a DC power supply supplied by Thurlby Thandar Instruments of Huntingdon UK, model Ex357tv and a polarity reversing switch.

The diffuser 111 was fabricated from clear 3 mm thick Macrolon polycarbonate sheet and was approximately 150 mm square. The diffusing effect was obtained by attaching two sheets of drawing film to the underside of the plate using 3M spraymount adhesive. This composite plate was drilled with a plurality of holes approximately 5 mm in diameter, each hole inclined so that its axis was directed towards the centre of the rotary table 104, which was 65 mm below the diffuser. Sixteen directional white 5 mm diameter LEDs 109 (Marl model 110147-01BC) with a 20 degree viewing angle were provided, arranged according to the tilted spiral pattern illustrated in FIG. 4 and mounted directly into the holes in the diffuser plate. In an alternative embodiment, the LEDs were all mounted vertically and a single plastic Fresnel lens was mounted directly beneath them to deflect the light towards the gem diamond.

A further 12 background LEDs 110 (Luxeon lumiled model LXHL-MWEC) were mounted in a circular pattern with a diameter of 110 mm on an aluminium alloy plate approximately 40 mm above the diffuser.

The directional LEDs 109 were controlled by the PC via a USB interface card model U3-LV by Labjack corporation of Lakeview Colo. USA, and a proprietary interface that allowed each individual directional LED to be driven with a current of between 0 and 20 mA. The background LEDs were similarly controlled, and wired in series so that they could be driven with a controlled current of between 0 and 350 mA.

The camera 105 was a Sony FCB-EX11DP colour camera module and incorporated a 10:1 zoom lens. The entrance pupil of this camera (which is not circular, but, depending on the aperture setting, is approximately trapezoidal) is located approximately 110 mm behind the front face of the camera when the camera was set to its longest focal length An additional doublet lens (63DQ16, supplied by Comar Instruments of Cambridge Uk) was mounted just below the diffuser plate in a Comar model 10 XE 16 lens cell, fitted into an 18 mm diameter hole drilled in the diffuser plate to form one assembly The lens was approximately 60.5 mm from the gem diamond 113, with the camera module approximately 15 mm above the doublet lens. The more curved side of the doublet lens faced the camera module.

The apparatus offered a field of view of approximately 3 mm×4 mm at the highest magnification, and offers an field of view of 9 mm×12 mm with minimal vignetting Larger fields of view may be obtained, but with some vignetting.

The doublet lens performs a dual role of forming an image of the gem diamond at infinity so that the camera module may form an image of it, and also of re-imaging the entrance pupil of the camera module, so that it is approximately 120 mm in front of the doublet lens, so that when reflected from the table of the gem diamond 113 the entrance pupil is, for small tilt angles, in the plane of the diffuser plate and thus matched to the illumination.

In practice, this matching was carried out empirically rather than by calculation, adjusting the relative position of the camera module and the diffuser/lens assembly until, as the turntable rotated, the specular reflection from the table facet of the gem diamond appeared to be illuminated uniformly without any obvious motion across the table.

The camera image was output in PAL format and displayed on an 8" LCD monitor manufactured by Lilliput. The video could also be captured as a digital video sequence using a Pinnacle 510 USB video capture unit connected to the PC.

The apparatus was used to demonstrate the attractiveness of a 0.67 carat round brilliant diamond inscribed with the Forevermark logo and a serial number using the following method.

The camera was set to an aperture of f/5.6 with an exposure time of 1/30 second and a gain of 0 db. All the directional LEDs 109 and the diffuse LEDs 110 were driven at a current of 10 mA and 250 mA respectively.

The diamond 113, supported in a ring and mounted in a ring holder 114 was placed on the rotary table 104. The magnification was set so that the diamond approximately filled the vertical field of view. Manual centring was carried out by the operator and the focus was adjusted. The magnification was then reduced so that more of the jewelry ring was visible The rotary table 104 was set to rotate and the diamond was first observed directly from the front of the apparatus. This was seen to be presented in an attractive fashion, demonstrating sparkles or scintillations in a manner that was considered to be natural and effective, and not contrived or artificial. The most attractive presentation was obtained for a rotation speed of 2-3 revolutions per minute, but other rotational speeds could be used.

Next, attention was drawn to the LCD screen where a similar but magnified view of the diamond and supporting jewelry was displayed. The magnification was then increased so that the diamond nearly filled the field of view, drawing attention to the diamond itself. It was found that a range of visual appearances could be obtained by adjusting the balance between the background and directional illumination. Scintillations or sparkles could be observed distributed throughout the diamond in an attractive but not obviously symmetrical pattern. Some scintillations were essentially a transition from dark to light (i.e. white) to dark again, but others could be characterised as a transition through the visible spectrum from blue to red or vice versa, the colours being most obvious at the blue and yellow-red ends of the spectrum. This is the phenomenon known as fire in the diamond trade.

In the course of the rotation the operator was able to identify times when a specular reflection was visible from the table facet. By switching the directional LEDs 109 off in sequence, it was possible to identify which LED was causing the reflection. This LED was left switched off so that no further specular reflections were seen in subsequent rotations.

Finally the diamond was brought to rest in the position where the specular reflection had been observed. The optical magnification was increased to its maximum value The lighting was then slowly switched, over the course of 1-2 seconds so that ultimately only the single directional LED that had been previously switched off was now on, revealing the Forevermark inscription on the table of the diamond. Some digital zoom may optionally be employed to allow the mark to be more easily read.

It was found that many other attractive effects could be generated including but not limited to:

Allowing the diamond to be viewed deliberately out of focus to introduce blurring then slowly moving it into focus.

Reducing the lens aperture (for example to f/8 or f/11) to reduce the overall intensity of the light and increase the amount of "Fire" that could be observed in each scintillation.

Allowing the turntable to rotate slowly or come to rest as the inscription was revealed to produce a range of contrast effects as the light source is scanned across the entrance pupil of the lens.

Deliberately operating the unit to reveal the mark with a mis-match between the illumination and entrance pupils to create the effect of a dark to bright transition travelling across the surface.

It was also possible to introduce extra dynamic effects into the scintillation effect by switching the LEDs on and off at a suitable rate, or using LEDs that could display different colours. However these effects could be considered to be contrived or unnatural and might be best employed sparingly if at all.

It was also found that fewer than 16 LEDs could be used effectively, for example 10. It was also found that it tended to be the LEDs nearer the centre that would reveal the mark, showing that operators would tend to place the jewelry into the apparatus with the table reasonably horizontal.

In a further experiment where the support member 102 was placed vertically with the rotary table 104 horizontal so that the imaging axis 107 and rotational axis 117 are coincident (as in FIG. 5), with the central LED omitted, it was found that a specular reflection from the table was quite often not seen, rendering the apparatus less reliable.

It will be appreciated that variations from the above described embodiments may also fall within the scope of the present invention. For example, the system has been described with reference to a rotary table on which a diamond can be placed. It will be appreciated that the illumination structure and/or camera may be rotated relative to the diamond, instead of the diamond being physically rotated, although the results tend to be more aesthetically pleasing if the diamond itself is rotated. As a further alternative, the directional LEDs could be activated in sequence to provide the effect of a rotating illumination structure.

In addition, it will be appreciated that it may be possible to use additional directional LEDs instead of the background LEDs and diffuser, although this may affect the balance between scintillations and background illumination, which may be less aesthetically pleasing.

The directional light sources have been described as directional LEDs 109 located behind holes or clear apertures 112 in the diffuser 111. It will be appreciated that any suitable arrangement for providing directional light may be used. In one arrangement, directional light may be provided by LEDs (or any suitable light source) located behind collimating lenses. These lenses may be incorporated or moulded preferably onto the upper surface of the diffuser. Preferably the lenses should be arranged so that the ray of light that illuminates the centre of the diamond should meet the curved surface of the lens at normal incidence.

Furthermore, the apparatus has been described with a base and generally vertical support member. It will be appreciated that other arrangements will be available in practice, as long as the necessary rotations between diamond, illumination structure and camera can be achieved, and as long as the camera can be focussed on the diamond. In practice, the elements (including the viewing screen) may be incorporated into a single, stand-alone instrument. Such an instrument may still have a large opening through which the diamond can be observed directly, so that the diamond can be viewed simultaneously on the screen and "in the flesh".

The invention claimed is:

1. Apparatus for viewing images of a gemstone, comprising:
   a support structure for supporting the gemstone at an observation position;
   an illumination structure arranged to illuminate the gemstone, the illumination structure comprising a plurality of directional light sources directed towards the observation position, the illumination structure being effectively rotatable relative to the support structure about a rotation axis by sequential operation of the directional light sources; and
   an imaging device for obtaining images of the gemstone at the observation position at a variety of effective rotational positions of the illumination structure, the imaging device having an imaging axis passing through the observation position;
   wherein the support structure is arranged so that the gemstone can be placed at the observation position in such a way that the normal to a selected facet of the gemstone is within a predetermined range of tilt angles from the rotation axis; and
   the arrangement of directional light sources is such that, for any tilt angle within the range, light from at least one of the directional light sources will be specularly reflected from the selected facet into the imaging device for at least one effective rotational position of the illumination structure.

2. The apparatus of claim 1, wherein a locus can be visualised on the illumination structure of a reversed ray reflected in the selected facet from the imaging device for a 360° effective rotation of the illumination structure with the facet at any given tilt angle, and wherein the directional light sources are arranged so that at least one of the directional light sources is located on the locus for every tilt angle within the range of tilt angles.

3. The apparatus of claim 1, wherein the directional light sources are arranged so that light sources on successive loci are advanced in phase by an angle such as 90° or 137.5° so as to produce a spiral pattern.

4. The apparatus of claim 1, wherein the illumination structure is arranged generally between the imaging device and the observation position, with a hole in the illumination structure to enable light to pass from the observation position to the imaging device.

5. The apparatus of claim 1, wherein the imaging axis and rotational axis are inclined to each other, for example at an angle between 0° and 45° or 0° and 5°.

6. The apparatus of claim 1, further comprising a display screen for displaying images obtained by the imaging device.

7. The apparatus of claim 1, in which all the elements are integrated in a stand-alone instrument.

8. The apparatus of claim 1, arranged so that an image of a mark inscribed on the selected facet of the gemstone is obtainable by the imaging device when light from one of the directional light sources is specularly reflected from the selected facet into the imaging device.

9. The apparatus of claim 8, further comprising a processor for analysing the images obtained by the imaging device and identifying which of the directional light source is specularly reflected from the selected facet into the imaging device so that the image of the mark can be obtained.

10. The apparatus of claim 9, wherein the processor is operatively connected to a control system for controlling the sequential operation of the directional light sources, and the control system is configured to ensure activation of the at least one directional light source specularly reflected into the imaging device for the image of the mark to be displayed to the user after the images illustrating the play of light in the gemstone have been displayed to the user.

11. The apparatus of claim 1, wherein the range of tilt angles is between 0° and 10° or between 0° and 5°.

12. Apparatus for generating and viewing images of the play of light in a loose or mounted gemstone and an inscribed mark on the gemstone in a single integrated unit, comprising:
   a support structure for supporting the gemstone in an observation position;
   an illumination structure for illuminating the gemstone in the observation position, the illumination structure comprising a plurality of directional light sources and a diffuse light source;
   a control system for causing sequential operation of the directional light sources in such a way as to cause effective rotation of the illumination structure relative to the support structure about a rotation axis;
   an imaging device for obtaining images of the gemstone in the observation position; and
   a display device for displaying the images of the gemstone to a user at a plurality of effective rotational positions of the illumination structure;
   wherein the support structure is arranged so that the gemstone can be placed at the observation position in such a way that the normal to a selected facet of the gemstone is within a range of tilt angles from the rotation axis; and
   wherein the arrangement of directional light sources is such that, for any tilt angle within the range, light from at least one of the directional light sources will be specularly reflected from the selected facet into the imaging device for at least one effective rotational position of the illumination structure.

13. A method for facilitating the visual appreciation of the play of light of a loose or mounted gemstone and a mark inscribed on a selected facet of the gemstone, the method comprising:
   illuminating the gemstone with a plurality of directional light sources;
   causing the directional light sources to operate sequentially so as to give the effect of illumination of the gemstone rotating about a rotation axis, the normal to the selected facet of the gemstone being within a range of tilt angles from the rotation axis;
   obtaining images of the gemstone as the effective illumination rotates; and
   displaying the images to a viewer;
   wherein the arrangement of directional light sources is such that, for any tilt angle within the range, light from at least one of the directional light sources is specularly reflected from the selected facet into the imaging device for at least one effective rotational position of the illumination.

14. The method of claim 13, the method further comprising displaying an image of the inscribed mark to the user by identifying and then operating the directional light source from which light is specularly reflected from the selected facet into the imaging device.

15. The method of claim 14, further comprising viewing the gemstone by eye as the illumination effectively rotates.

* * * * *